US008658830B2

(12) United States Patent
Brietzke et al.

(10) Patent No.: US 8,658,830 B2
(45) Date of Patent: *Feb. 25, 2014

(54) METHOD TO RECOVER ORGANIC TERTIARY AMINES FROM WASTE SULFURIC ACID

(75) Inventors: Stephan Brietzke, Wiesbaden (DE); Peter Groer, Babenhausen (DE); Carl Christoph Mollenkopf, Frankfurt (DE)

(73) Assignee: Nutrinova Nutrition Specialties & Food Ingredients GmbH, Sulzbach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/640,328

(22) PCT Filed: Apr. 13, 2011

(86) PCT No.: PCT/EP2011/055788
§ 371 (c)(1),
(2), (4) Date: Dec. 3, 2012

(87) PCT Pub. No.: WO2011/131530
PCT Pub. Date: Oct. 27, 2011

(65) Prior Publication Data
US 2013/0096350 A1    Apr. 18, 2013

(30) Foreign Application Priority Data
Apr. 19, 2010 (EP) .................................. 10160272

(51) Int. Cl.
*C07C 209/86* (2006.01)

(52) U.S. Cl.
USPC .......................................... 564/497; 564/498

(58) Field of Classification Search
USPC .................................................. 564/497, 498
See application file for complete search history.

(56) References Cited

U.S. PATENT DOCUMENTS

| 3,151,163 A * | 9/1964 | Nussbaum ................... 564/481 |
| 8,496,905 B2 * | 7/2013 | Brietzke et al. .............. 423/549 |

FOREIGN PATENT DOCUMENTS

| CN | 1883790 | 12/2006 | |
| DE | 3522470 A | 1/1987 | |
| DE | 3545196 A1 * | 6/1987 | ............. C01B 17/90 |
| DE | 4416571 C1 | 12/1995 | |
| DE | 10146689 A | 4/2003 | |
| WO | WO 2007/079944 A1 | 7/2007 | |

OTHER PUBLICATIONS

International Search Report for PCT/EP2011/055788 mailed Jun. 17, 2011.

* cited by examiner

*Primary Examiner* — Brian J Davis

(57) ABSTRACT

The present invention describes a method to recover organic tertiary amines from waste sulfuric acid comprising the following steps:
  a) reacting i) waste sulfuric acid comprising organic tertiary amines with ii) ammonia in an amount sufficient to obtain a pH of 9.5 or higher and
  b) separating the organic tertiary amines from the reaction mixture obtained in step a) wherein during the separation the pH of the reaction mixture is adjusted at a pH of 9.5 or higher.

19 Claims, 1 Drawing Sheet

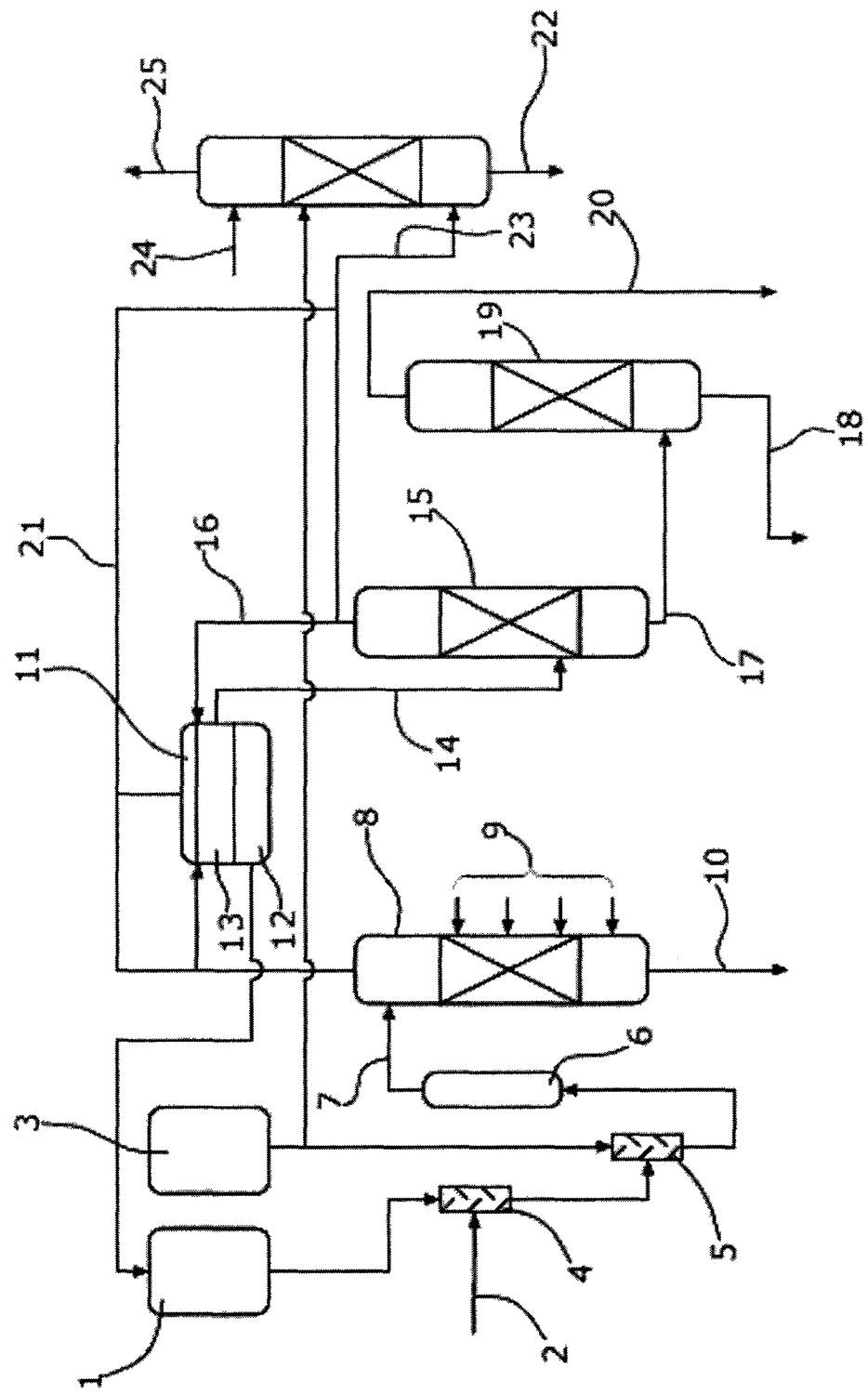

METHOD TO RECOVER ORGANIC TERTIARY AMINES FROM WASTE SULFURIC ACID

This application is a national stage application of PCT/EP2011/055788 filed Apr. 13, 2011, which claims priority to EP Application No. 10160272.0, filed Apr. 19, 2010, the entire contents and disclosures of which are hereby incorporated by reference.

The invention relates to a method to recover organic tertiary amines from waste sulfuric acid as well as the use of said method to produce ammonium sulfate.

Waste sulfuric acid containing organic tertiary amines is obtained in many chemical plants and is a waste product from various chemical reactions.

The organic tertiary amines do have an economic value and as a consequence, it is desirable to recover the tertiary amines from the waste sulfuric acid. Further, waste sulfuric acid can be converted to ammonium sulfate which is commonly used as a fertilizer. However, it is a requirement for a good inorganic fertilizer that the total amount of organic compounds (TOC) is as low as possible.

It is known that waste sulfuric acid under reclamation of $SO_2$ can be treated thermally, whereby the contained amines are however lost. The production of $SO_2$ to the detriment of the contained amines is economically disadvantageous.

DE 101 46 689 A describes a method to recover organic amines from catalysts containing amines by distillative separation.

DE 35 22 470 A describes the recovery of amine- and metallic components in polyphenylene ether synthesis by separation using caustic soda.

DE 44 16 571 describes the recovery of amine from acidic solutions by the addition of alkali bases followed by distillation.

CN 1883790 describes the recovery of amines by neutralization with inorganic bases of oxide origin (NaOH, KOH, $Ca(OH)_2$, $CaCO_3$). In so doing the created sulfates must either be disposed of or processed using large amounts of energy (evaporation, drying) in order to obtain a usable by-product. Also, due to the mole masses of the oxide, bases require relatively large mass shares. In case of calcium bases, the created calcium sulfate already precipitates during the reaction and therefore, the suspension must either be diluted or thoroughly blended at substantial costs.

DE 35 45 196 A1 discloses a process to recover tertiary aliphatic amines from waste sulfuric acid with ammonia. However, the yield of the tertiary amines recovered by the process disclosed in DE 35 45 196 A1 is too low and, as a consequence, the total amount of organic compounds which remain in the ammonium sulfate obtained from the process is too high. Thus, the process disclosed in the prior art requires a further purification step in order to reduce the amount of organic compounds in the dry ammonium sulfate to an acceptable level, i.e. a total amount of organic compounds (TOC), preferably of less than 1, more preferably less than 0.5 weight percent based on the dried ammonium sulfate obtained by the process. The TOC is determined in that a sample is oxidized and the amount of generated $CO_2$ is measured. The TOC can be determined according to the standard method DIN EN 1484-H3. Further, for an acceptable fertilizer it is particular important to keep the amount of organic tertiary amine in the ammonium sulfate composition as low as possible. Additionally, the process disclosed in DE 35 45 196 A1 does not recover the economically valuable tertiary amines from the waste sulfuric acid in a sufficient amount.

Therefore, it was an object of the present invention to overcome the problems present in the prior art and in particular, it was an object to significantly increase the yield of tertiary amines recovered from waste sulfuric acid. Further, it was an object to significantly reduce the total amount of organic compounds in the ammonium sulfate obtained from the process to recover the tertiary amine.

It has surprisingly been found that the problems associated with the methods to recover organic tertiary amines from waste sulfuric acids in the prior art can be solved by a method which uses ammonia and which controls the pH during the separation process.

The invention accordingly provides a method to recover organic tertiary amines from waste sulfuric acid comprising the following steps:

a) reacting
   i) waste sulfuric acid comprising organic tertiary amines with
   ii) ammonia in an amount sufficient to obtain a pH of 9.5 or higher and
b) separating the organic tertiary amines from the reaction mixture obtained in step a) wherein during the separation the pH of the reaction mixture is adjusted to a pH of 9.5 or higher.

The solution to the above-mentioned problems is surprising since in general to release amines from their ammonium salts, bases need to be used having a basicity of an order of magnitude higher than the corresponding amines. This applies, for example, to the bases described in CN 1883790 or DE-C-44 16 571.

Ammonia, on the other hand, has a comparable or lower basicity than the amines to be reclaimed such as triethylamine and many other amines.

In principle all tertiary amines are suited as organic amines to be recovered from the waste sulfuric acid by the method according to the present invention. The tertiary amines form corresponding hydrogen sulfates (below also referred to as organyl ammonium hydrogen sulfate) with sulfuric acid. Preferred tertiary amines are especially those comprising up to 20 carbon atoms, in particular up to 12 carbon atoms per nitrogen atom. Examples of amines which can be recovered from waste sulfuric acid by the method according to the present invention are selected from the group comprising trimethylamine, triethylamine, diethylpropylamine, tri-n-propylamine, triisopropylamine, ethyldiisopropylamine, tri-n-butylamine, triisobutylamine, tricyclohexylamine, ethyldicyclohexylamine, N,N-dimethylaniline, N,N-diethylaniline, benzyldinmethyla mine, pyridine, substituted pyridines such as picoline, lutidine, cholidine or methylethylpyridine, N-methylpiperidine, N-ethylpiperidine, N-methylmorpholine, N,N-dimethylpiperazine, 1,5-diazabicyclo[4.3.0]-non-5-en, 1,8-diazabicyclo-[5.4.0]-undec-7-en, 1,4-diazabicyclooctane, tetramethylhexamethylendia mine, tetramethylethylendiamine, tetramethylpropylendiamine, tetramethylbutylendiamine, 1,2-dimorpholylethan, pentamethyldiethyltriamine, pentaethyldiethylentriamine, pentamethyldipropylentriamine, tetramethyldi-aminomethane, tetrapropyldiaminomethane, hexamethyltriethylentetramine, hexamethyltripropylenetetramine, diisobutylentriamine and triisopropylen-triamine.

Especially preferred is triethylamine.

Ammonia is an inexpensive, easily available chemical basic product and due to its low molecular weight has a highly favorable mass balance.

Ammonia can be used in gaseous or liquid form. According to the invention the partial pressure of the ammonia to be used can be between 0.1 and 300 bar and is limited only by the compressive strength of the used equipment. Ammonia can be used neat or as a mixture with other gases.

Ammonia can be used as a solution in other solvents, preferably as an aqueous solution. The aqueous solution can be obtained commercially or be produced directly from the reaction by introducing gaseous or liquid ammonia in water. The heat of solution can either be removed or retained by transferring the heated solution to the following reaction step. To avoid the exhalation of ammonia it is preferred to work at elevated pressure, e.g. a pressure of higher than 1 bar, preferably 1,5 to 10 bar. In step a) of the method to recover organic tertiary amines from waste sulfuric acid of the present invention, ammonia in gaseous or dissolved form is brought to the reaction with waste sulfuric acid comprising organic tertiary amines.

The ammonia is mixed with the waste sulfuric acid in an amount sufficient to obtain a pH of 9.5 or higher. According to a preferred embodiment of the method of the present invention the pH in step a) is preferably ranging from 9.8 to 12, i.e. the ammonia is added to the waste sulfuric acid in an amount sufficient to obtain a pH ranging from 9.8 to 12, more preferably from 10, or higher than 10, to 11.5.

During the reaction of waste sulfuric acid with ammonia, first the free sulfuric acid is neutralized followed by conversion of organyl ammonium hydrogen sulfate to the corresponding amines. The reaction can be conducted batchwise, e.g. in an agitating machine or continuously in a pump reactor with or without agitation means. In the latter case, a static mixer is also suited, which in turn can be equipped with a temperature equalizer.

In a preferred embodiment of the method according to the present invention the reaction in step a) is conducted in a plug flow reactor. The plug flow reactor is preferred since the reaction can be conducted at elevated pressure and elevated temperature.

The reaction according to step a) of the method of the present invention is preferably conducted under an elevated pressure, preferably under pressure ranging from 2 to 12 bar, more preferably from 7 to 10 bar.

The temperature at which the reaction in step a) is conducted is preferably ranging from 95 to 150° C., more preferably 100 to 140° C., most preferably from 110 to 130° C.

In order to avoid precipitation of ammonium sulfate by exceeding the solubility limit during or after the reaction, water can be added to the reaction mixture. This can be done by diluting the employed waste sulfuric acid with water before the reaction, by adding water during the reaction or by diluting the obtained ammonium sulfate solution after completion of the reaction.

The produced reaction heat can be removed using typical cooling devices known to the person skilled in the art. However, according to a preferred embodiment, the released reaction heat of the reaction of step a) is used in separation step b) for the distillative elimination of the organic tertiary amines. In case the reaction in step a) has been conducted under pressure and elevated temperature the expanded reaction mixture can be directly conveyed to the distillation column. Preferably the method is conducted at temperatures which work at the boiling point of the free amine or if present, the boiling temperature of the amine/water azeotrope or above. In case the reaction heat is not sufficient for distillation an additional heating may be required. For example, in the case of triethylamine the preferred temperature is between 75 and 105° C. at 1 bar.

Further, according to a preferred embodiment of the present method, the energy released in step a) is at least partially used to evaporate the water in the concentration process in order to produce the solid ammonium sulfate, i.e. the reaction heat can be used to evaporate the water from the aqueous ammonium sulfate solution obtained by the method of the present invention.

Preferably an excess of ammonia is mixed with the waste sulfuric acid in order to achieve the required pH of 9.5 or higher.

Solutions which are suitable as waste sulfuric acids contain preferably 0.1 to 100% by weight of the respective organyl ammonium hydrogen sulfate. Solutions may also contain free sulfuric acid and water. A typical waste sulfuric acid can for example, comprise 35% by weight triethylammonium hydrogen sulfate, 45% by weight sulfuric acid, 16% by weight water and minor amounts of organic components.

In step b) of the method of the present invention the organic tertiary amines are separated from the reaction mixture obtained in step a) wherein during the separation the pH of the reaction mixture is adjusted at a pH of 9.5 or higher. Preferably the pH is adjusted to a range from 9.8 to 12, more preferably from 10, or higher than 10, to 11.5.

The separation of the released amines from the reaction mixture obtained in step a) can be done by distillation, extraction and through phase separation. Distillative separation is especially advantageous for amines with a low boiling point and amines with good water solubility. The above applies especially to amines that form an azeotrope with water. Distillative separation can be done directly from the reaction vessel or in a two stage apparatus.

According to a preferred embodiment the thermal energy of the products obtained at the still head of the distillation column may be used to heat the feed flow, e.g. the ammonia feed or the feed comprising the reaction mixture.

Low solubility amines in ammonium sulfate solution can be obtained through phase separation. Also, the ammonium sulfate solution can be extracted with a suitable solvent. Preferably, the organic tertiary amine is separated from the reaction mixture by extraction with an organic liquid, preferably a liquid hydrocarbon, more preferably an aliphatic liquid hydrocarbon comprising at least 6 carbon atoms, especially octane. However, the type of solvent is only limited by the stability of the used substances, the solubility of the ammonium sulfate solution and the following separability from the extracted amine.

The methods for the separation of the released amines can be applied individually or in combination.

According to an especially preferred method of the present invention the organic tertiary amine, preferably triethylamine, is separated from the reaction mixture obtained in step a) in a distillation column. In order to maintain a pH of 9.5 or higher during the separation in a distillation column, ammonia is preferably added to the distillation column. Preferably during the distillation ammonia is added to the distillation column in a counter flow to the reaction mixture obtained in step a).

According to a preferred embodiment, during the distillation the reaction mixture obtained in step a) is continuously fed to the upper part of a distillation column and the ammonia is continuously fed at the lower part or the middle part of the distillation column. The position of the ammonia feed to the distillation column can be used to control the pH of the reaction mixture to be separated during the separation process. The amount of ammonia and consequently the adjusted pH-value influence the capacity of the column with respect to separation of the tertiary amines from the aqueous ammonium sulfate solution. The closer the ammonia feed is to the bottom of the distillation column the higher the pH of the reaction mixture in the bottom of the column. The pH value referred to in step b) of the method of the present invention is in case of a separation in a distillation column, the minimum pH value measured in the column between the feed of the reaction mixture and the feed of the ammonia.

Likewise, the position of the ammonia feed to the distillation column also influences the pH value of the aqueous solution comprising ammonium sulfate in the bottom of the column. In a preferred embodiment, the ammonia feed is placed at a position of the distillation column such that the aqueous solution, which is essentially free of the organic tertiary amine, in the lower part of the column has a pH ranging from 5 to 7.

Excess of ammonia can be reintroduced to the process according to the invention. This can be done purposely, e.g. by washing the exhaust containing ammonia with the employed waste sulfuric acid.

According to a preferred embodiment the organic tertiary amine, preferably triethylamine, is recovered in a yield of at least 99.0%, more preferably 99.5%.

According to a further embodiment of the present invention the method of the invention is used to produce ammonium sulfate. The ammonium sulfate solution obtained by the method of the invention represents a quickly recoverable, easily dosable, valuable nitrogen fertilizer. No additional processing is required prior to use. The ammonium sulfate content of the solution can be set as desired by the water content of the used waste sulfuric acid, the addition of water before, during or after the reaction and/or distillative removal of water taking into account the solubility limit of ammonium sulfate in water. Also possible is complete water removal using current methods such as distillation or spray drying, whereby ammonium sulfate is produced as a solid that can be used as a fertilizer.

According to a preferred embodiment, the method of the invention further comprises a dewatering step of the recovered tertiary amine which can optionally be followed by a further distillation of the dewatered amine.

A preferred embodiment of the process of the invention is illustrated by means of the following FIG. 1. FIGURE measures known per se, e.g. addition of stabilizer, are not shown.

BRIEF DESCRIPTION OF THE DRAWING

FIG. 1 shows a schematic diagram of a method to recover triethylamine from waste sulfuric acid comprising triethylamine.

| Reference Signs | |
|---|---|
| 1 | water reservoir |
| 2 | ammonia supply |
| 3 | waste sulfuric acid reservoir |
| 4 | first plug flow reactor |
| 5 | second plug flow reactor |
| 6 | pipe reactor |
| 7 | feed for the reaction mixture |
| 8 | distillation column |
| 9 | ammonia feed |
| 10 | flow for the ammonium sulfate solution |
| 11 | separator |
| 12 | water phase |
| 13 | organic phase |
| 14 | feed for the organic phase |
| 15 | dewatering column |
| 16 | feed for an azeotrope of water and tertiary amine |
| 17 | flow for the tertiary amine |

-continued

| Reference Signs | |
|---|---|
| 18 | flow for high boiler |
| 19 | distillation column |
| 20 | flow for the purified tertiary amine |
| 21 | ammonia comprising gases |
| 22 | flow of washing liquid |
| 23 | ammonia supply |
| 24 | water supply |
| 25 | exhaust gas |

Gaseous ammonia is added via ammonia supply (2) to a first plug flow reactor (4) and diluted with water from a water reservoir (1). The aqueous ammonia solution is conveyed to a second plug flow reactor (5) where it is brought into contact with the waste sulfuric acid from the waste sulfuric acid reservoir (3). The waste sulfuric acid and the aqueous ammonia solution are reacted in a pipe reactor (6) and subsequently conveyed to a distillation column (8). The distillation column (8) has different ammonia feeds (9) which can be used to adjust the pH value during the separation process in the column. In the bottom of column (8) the ammonium sulfate solution is obtained which can be released from column (8) by flow (10). The triethylamine-water azeotrope is distilled off and conveyed to the phase separator (11) wherein the azeotrope is separated in a water phase (12) and an organic phase (13) which comprises the triethylamine. The organic phase is fed via feed (14) to the dewatering column (15). The azeotrope of water and triethylamine distilled off in the dewatering column (15) is conveyed via feed (16) to the separator (11). The triethylamine obtained at the bottom of dewatering column (15) is conveyed via flow (17) to distillation column (19). In distillation column (19) the purified triethylamine is distilled off via flow (20). From the bottom of distillation column (19) high boiling organic residues can be separated via flow (18). Ammonia containing gases are conveyed via line (21) and (23) to a column with a flow (22) and a water supply (24) and a supply from the waste sulfuric acid reservoir (3). Exhaust gas which is essentially free from ammonia can be released from the column via line (25).

The ammonia containing washing liquid released via flow (22) can be reintroduced in the process.

a) Separation of triethylamine in a Distillation Column 195 g of ammonia mixed with 755 g of water is reacted with 900 g of waste sulfuric acid consisting of 148 g water, 400 g $H_2SO_4$ and 334 g triethylammoniumhydrogensulfate (equivalent to 171 g of triethylamine) and additional 700 g of water.

The reaction mixture exhibits a pH value of 10. Subsequently, the reaction mixture is fed to the upper part of a distillation column while at the lower part of the distillation column ammonia is fed to the column in a counter flow fashion in order to keep the pH of the reaction mixture above 10. The pH value of the mixture in the column can be adjusted by the position of the ammonia feed at the lower part of the column.

Different pH values have been adjusted and the amount of triethylamine recovered has been determined. The weight-% of triethylamine recovered is based on the total weight of triethylamine present in the waste sulfuric acid.

TABLE 1

Examples 1 and 2 and Comparative Examples 3 to 5

| Example | pH-value determined during separation | weight-% of triethylamine recovered |
|---|---|---|
| 1 (according to the invention) | 9.5 | 93.0 |
| 2 (according to the invention) | 10.1 | 99.0 |
| 3 (comparative) | 9.0 | 68.0 |
| 4 (comparative) | 7.0 | 2.0 |
| 5 (comparative example 2 of DE 35 45 196) | not mentioned | 92.6% | b) Separation of triethylamine by Extraction with dichloromethane 530 g ice and 870 g of waste sulfuric acid consisting of 145 g water, 393 g $H_2SO_4$ and 308 g triethylammoniumhydrogensulfate (=equivalent to 158 g of triethylamine) are added to 683 g of an aqueous ammonia solution (25 wt.-% ammonia). The reaction mixture obtained shows a pH of 7.2. The mixture is subsequently divided in two equal parts (part 1 and part 2).

To part 2 54 g of an aqueous ammonia solution (25 wt.% ammonia) is added to obtain a pH of 10.1. Part 1 and part 2 are each 3 times extracted with 200 g dichloromethane at 25° C. The organic phases are subsequently dried with sodium sulfate, filtered and washed with dichloromethane to obtain 750 g of a dichloromethane solution.

The amount of extracted triethylamine is determined by gas chromatography.

TABLE 2

Separation of triethylamine by extraction at different pH-values

| Example | pH adjusted to | Triethylamine recovered in wt-% |
|---|---|---|
| Part 1 (comparative) | 7.2 | 1.75 |
| Part 2 (according to the invention) | 10.1 | 80.6 |

The invention claimed is:

1. Method to recover organic tertiary amines from waste sulfuric acid comprising the following steps:
   a) reacting i) waste sulfuric acid comprising organic tertiary amines with ii) ammonia in an amount sufficient to obtain a pH of 9.5 or higher and
   b) separating the organic tertiary amines from the reaction mixture obtained in step a) wherein during the separation the pH of the reaction mixture is adjusted to a pH of 9.5 or higher.

2. Method according to claim 1 wherein the organic tertiary amine is separated from the reaction mixture obtained in step a) in a distillation column.

3. Method according to claim 2 wherein during the distillation ammonia is added to the distillation column.

4. Method according to claim 3 wherein during the distillation ammonia is added to the distillation column in a counter flow to the reaction mixture obtained in step a).

5. Method according to claim 4 wherein during the distillation the reaction mixture obtained in step a) is continuously fed to the upper part of a distillation column and the ammonia is continuously fed to the lower part or the middle part of the distillation column.

6. Method according to claim 5 wherein the ammonia feed to the distillation column is positioned such that the aqueous solution which is essentially free of organic tertiary amine and which comprises the ammonium sulfate in the lower part of the column has a pH ranging from 5 to 7.

7. Method according to claim 1 wherein the organic tertiary amine is separated from the reaction mixture by extraction with an organic liquid.

8. Method according to claim 1 wherein the pH in step a) and/or step b) ranges from 9.8 to 12.

9. Method according to claim 1 wherein the organic tertiary amine is triethylamine.

10. Method according to claim 1 wherein the organic tertiary amine is recovered in a yield of at least 99.0%.

11. Method according to claim 1 wherein the waste sulfuric acid comprises 0.1 to 100% by weight of the organic tertiary amine as organyl ammonium hydrogen sulfate.

12. Method according to claim 1 wherein the released reaction heat of the reaction in step a) is used in the separation step b) for the separation of the organic tertiary amine.

13. Method according to claim 1 wherein step a) is conducted under elevated pressure.

14. Method according to claim 1 wherein the reaction in step a) is conducted at a temperature ranging from 90 to 150° C.

15. Method according to claim 1 wherein step a) is conducted under a pressure ranging from 2 to 12 bar.

16. Method according to claim 1 wherein step a) is conducted under a pressure ranging from 7 to 10 bar.

17. Method according to claim 1 wherein the reaction in step a) is conducted at a temperature ranging from 90 to 150° C.

18. Method according to claim 1 wherein the reaction in step a) is conducted at a temperature ranging from 100 to 140° C.

19. Method according to claim 1 wherein the reaction in step a) is conducted at a temperature ranging from 110 to 130° C.

* * * * *